United States Patent
Pu et al.

(10) Patent No.: US 8,992,436 B2
(45) Date of Patent: Mar. 31, 2015

(54) RESPIRATION MONITORING USING RESPIRATION RATE VARIABILITY

(75) Inventors: Yachuan Pu, Minneapolis, MN (US); Yi Zhang, Blaine, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2080 days.

(21) Appl. No.: 11/514,423

(22) Filed: Sep. 1, 2006

(65) Prior Publication Data

US 2007/0073181 A1 Mar. 29, 2007

Related U.S. Application Data

(60) Provisional application No. 60/717,654, filed on Sep. 16, 2005.

(51) Int. Cl.
*A61B 5/08* (2006.01)

(52) U.S. Cl.
CPC .................................. *A61B 5/0816* (2013.01)
USPC ......................................................... 600/529

(58) Field of Classification Search
USPC ................................................. 600/529–543
See application file for complete search history.

(56) References Cited

U.S. PATENT DOCUMENTS

| | | |
|---|---|---|
| 4,562,841 A | 1/1986 | Brockway et al. |
| 5,036,849 A | 8/1991 | Hauck et al. |
| 5,133,353 A | 7/1992 | Hauser |
| 5,179,945 A | 1/1993 | Van Hofwegen et al. |
| 5,203,348 A | 4/1993 | Dahl et al. |
| 5,230,337 A | 7/1993 | Dahl et al. |
| 5,284,136 A | 2/1994 | Hauck et al. |
| 5,313,953 A | 5/1994 | Yomtov et al. |
| 5,314,459 A | 5/1994 | Swanson et al. |
| 5,318,597 A | 6/1994 | Hauck et al. |
| 5,360,442 A | 11/1994 | Dahl et al. |
| 5,366,496 A | 11/1994 | Dahl et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,540,727 A | 7/1996 | Tockman et al. |
| 5,545,202 A | 8/1996 | Dahl et al. |
| 5,603,732 A | 2/1997 | Dahl et al. |
| 5,620,466 A | 4/1997 | Haefner et al. |
| 5,662,688 A | 9/1997 | Haefner et al. |
| 5,836,987 A | 11/1998 | Baumann et al. |
| 5,916,243 A | 6/1999 | KenKnight et al. |
| 6,026,320 A | 2/2000 | Carlson et al. |
| 6,044,298 A | 3/2000 | Salo et al. |
| 6,055,454 A | 4/2000 | Heemels |

(Continued)

*Primary Examiner* — Michael D'Angelo
*Assistant Examiner* — Christian Jang
(74) *Attorney, Agent, or Firm* — Seager, Tufte & Wickhem, LLC

(57) ABSTRACT

Systems and methods provide for detecting respiration disturbances and changes in respiration disturbances, preferably by detecting variability in one or more respiration parameters. Respiration rate variability is determined for a variety of diagnostic and therapeutic purposes, including disease/disorder detection, diagnosis, treatment, and therapy titration. Systems and methods provide for generating a footprint, such as a two- or three-dimensional histogram, representative of a patient's respiration parameter variability, and generating one or more indices representative of quantitative measurements of the footprint.

30 Claims, 13 Drawing Sheets

(56) References Cited

U.S. PATENT DOCUMENTS

| | | |
|---|---|---|
| 6,076,015 A | 6/2000 | Hartley et al. |
| 6,360,127 B1 | 3/2002 | Ding et al. |
| 6,454,719 B1 * | 9/2002 | Greenhut .................. 600/484 |
| 6,597,951 B2 | 7/2003 | Kadhiresan et al. |
| 6,601,055 B1 * | 7/2003 | Roberts ...................... 706/45 |
| 6,718,197 B1 * | 4/2004 | Carlson et al. ............ 600/515 |
| 7,267,652 B2 * | 9/2007 | Coyle et al. ................ 600/538 |
| 2002/0002327 A1 * | 1/2002 | Grant et al. ................ 600/324 |
| 2002/0082867 A1 * | 6/2002 | MacCarter et al. ............ 705/2 |
| 2002/0143264 A1 | 10/2002 | Ding et al. |
| 2004/0077934 A1 * | 4/2004 | Massad .................... 600/300 |
| 2004/0111040 A1 | 6/2004 | Ni et al. |
| 2005/0043644 A1 * | 2/2005 | Stahmann et al. .......... 600/529 |
| 2005/0061320 A1 | 3/2005 | Lee et al. |

* cited by examiner

Hospitalized CHF Patient - At Discharge

RESPIRATION MONITORING USING RESPIRATION RATE VARIABILITY

RELATED APPLICATIONS

This application claims the benefit of Provisional Patent Application Ser. No. 60/717,654, filed on Sep. 16, 2005, to which priority is claimed pursuant to 35 U.S.C. §119(e) and which is hereby incorporated herein by reference.

FIELD OF THE INVENTION

The present invention relates generally to respiration detection and monitoring and, more particularly, to use of respiration rate variability and a footprint of same to detect, monitor, predict, and/or treat a patient condition.

BACKGROUND OF THE INVENTION

Disordered breathing is a common symptom that accompanies acute heart failure in a large number of individuals. Common forms of such disordered breathing include dyspnea, Cheyne-Stokes respiration, and sleep disordered breathing, such as sleep apnea and hypopnea. Disordered breathing may be caused by a wide spectrum of respiratory conditions involving the disruption of the normal respiratory cycle. Although disordered breathing often occurs during sleep, the condition may also occur while the patient is awake. Respiratory disruption can be particularly serious for patients concurrently suffering from cardiovascular deficiencies, such as heart failure. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, and periodic breathing, including Cheyne-Stokes respiration (CSR). Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration cycles have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Periodic breathing is characterized by cyclic respiratory patterns that may exhibit rhythmnic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with heart failure (HF) and is associated with an increased risk of accelerated HF progression. Because of the cardiovascular implications, detection, monitoring, and treatment for respiration-related disorders is of particular interest.

SUMMARY OF THE INVENTION

The present invention is directed to systems and method for assessing patient conditions based on patient respiration. Respiration and related parameters such as respiration rate and tidal volume, for example, may be used to detect, evaluate, and treat patient conditions, such as heart failure, periodic breathing, or sleep disordered breathing. Systems and methods of the present invention provide for obtaining a respiration-modulated signal representative of patient breaths and generating a footprint representative of the patient's respiration rate variability using the respiration-modulated signal. One or more indices representative of quantitative measurements of the footprint may be generated.

According to embodiments of the present invention, a respiration-modulated signal representative of patient breaths is obtained from which a respiration rate (RR) is computed. A difference of respiration rate ($\Delta RR$) between adjacent breaths is computed. A footprint representative of the patient's respiration rate variability is generated using $\Delta RR$. One or more indices are generated using the footprint.

The respiration-modulated signal may be obtained for a predetermined duration of time, such as 24 hours. The respiration-modulated signal may be obtained during a predetermined physiological state of the patient, such as during a state of patient activity, a sleep state of the patient or a state of patient wakefulness.

The one or more indices may comprise a feature of the footprint, a pattern of the footprint, an area of the footprint, a location of the footprint, a shape of the footprint, a contour of the footprint or a region of the footprint, such as an ectopic island of the footprint. Other indices include a conditional distribution developed from the footprint, a respiration rate histogram developed from the footprint, a respiration rate variability histogram developed from the footprint, and a mapping of the footprint to one or more patient states, for example. The one or more patient states may include patient activity, time of day, sleep, and wakefulness.

Embodiments of the present invention may further provide for detecting, tracking and predicting a patient condition, such as disordered breathing, using the footprint and the one or more indices. The disordered breathing condition may include one or more of sleep disordered breathing, dyspnea, and Cheyne-Stokes respiration, for example. Embodiments of the present invention may also provide for one or more of detecting, tracking and predicting a heart failure condition of the patient using the footprint and the one or more indices. For example, a heart failure decompensation episode of the patient may be detected, tracked and/or predicted using the footprint and the one or more indices.

An output signal based on the footprint and the one or more indices may be generated. One or more statistical analyses may be performed on the footprint, and one or more indices may be generated based on the one or more statistical analyses. Pattern recognition analyses may be performed on the footprint, and one or more indices may be generated based on recognized patterns.

Embodiments of the present invention may provide for adjusting or titrating a therapy delivered to the patient based on the footprint and the one or more indices. The therapy delivered to the patient may include one or more of a cardiac stimulation therapy, a respiration therapy, and a drug therapy. Effectiveness of a therapy delivered to the patient based on the footprint and the one or more indices may be determined and monitored. Embodiments may provide for discriminating between stable and worsening heart failure status of the patient using on the footprint and the one or more indices. A physician or the patient may be alerted based on the footprint and the one or more indices. Information may be communicated to a patient-external system, such as a programmer, personal communicator or a networked patient management system, based on the footprint and the one or more indices.

According to embodiments, a footprint of the present invention represents a two-dimensional construct, and methods of the present invention may involve adding a third dimension to the footprint. For example, the third dimension added to the footprint may be indicated using a color scheme superimposed on the two-dimensional construct. The third dimension added to the footprint may be indicated by graphical features or indicia extending from a two-dimensional plane of the construct into a plane orthogonal of the two-dimensional plane. The third dimension may be representative of tidal volume, a duration of time in which the patient is in a particular respiration pattern or a frequency of occurrence of a particular respiration pattern, for example.

One or both of the footprint and the one or more indices may be displayed or plotted. In the case of a third dimension being added to the footprint, one or both of the three-dimensional footprint and the one or more indices may be displayed or plotted.

In accordance with embodiments of the present invention, cardiac signals representative of the patient's cardiac electrical activity may be obtained. A cardiac activity footprint representative of the patient's heart rate variability may be generated using the cardiac signals, and one or more indices representative of quantitative measurements of the cardiac activity footprint may be generated. The respiration rate variability (RRV) footprint and the cardiac activity footprint may be combined to assess the patient's cardio-respiratory function. A cardio-respiratory function index may be developed using the RRV footprint and the cardiac activity footprint. A cardio-respiratory function index may be computed, for example, as a ratio of an area of the RRV footprint and an area of the cardiac activity footprint.

According to embodiments, a system of the present invention includes a medical device comprising sensing circuitry. Detection circuitry is disposed in the medical device and coupled to the sensing circuitry. The detection circuitry is configured to detect patient respiration. A processor is coupled to the detection circuitry. The processor is configured to generate a footprint representative of the patient's respiration rate variability using a respiration-modulated signal developed by the detection circuitry and generate one or more indices representative of quantitative measurements of the footprint. Systems of the present invention may implement one or more of the processes described above.

The processor may be disposed in a patient-external system, such as a programmer, personal communicator, or a networked patient management system. The medical device may also be disposed in a patient-external system. In other configurations, the medical device may be an implantable medical device, and the processor may be disposed in an implantable housing or a patient-external device or system.

The system may include a user interface configured to plot or display the footprint and the one or more indices, if desired. The sensing circuitry may include one or more sensors configured to sense a respiration-modulated physiological signal. Suitable sensors include a transthoracic impedance sensor, a minute ventilation sensor, an accelerometer, a pressure sensor, a respiratory band (e.g., elastic bands) sensing arrangement, a cardiac sensor (e.g., ECG sensor), electromyogram (EMG) sensor, and/or air flow sensor such as that of a positive airway pressure device (e.g., continuous positive airway pressure device) or a ventilator, for example.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figures 1, 2:
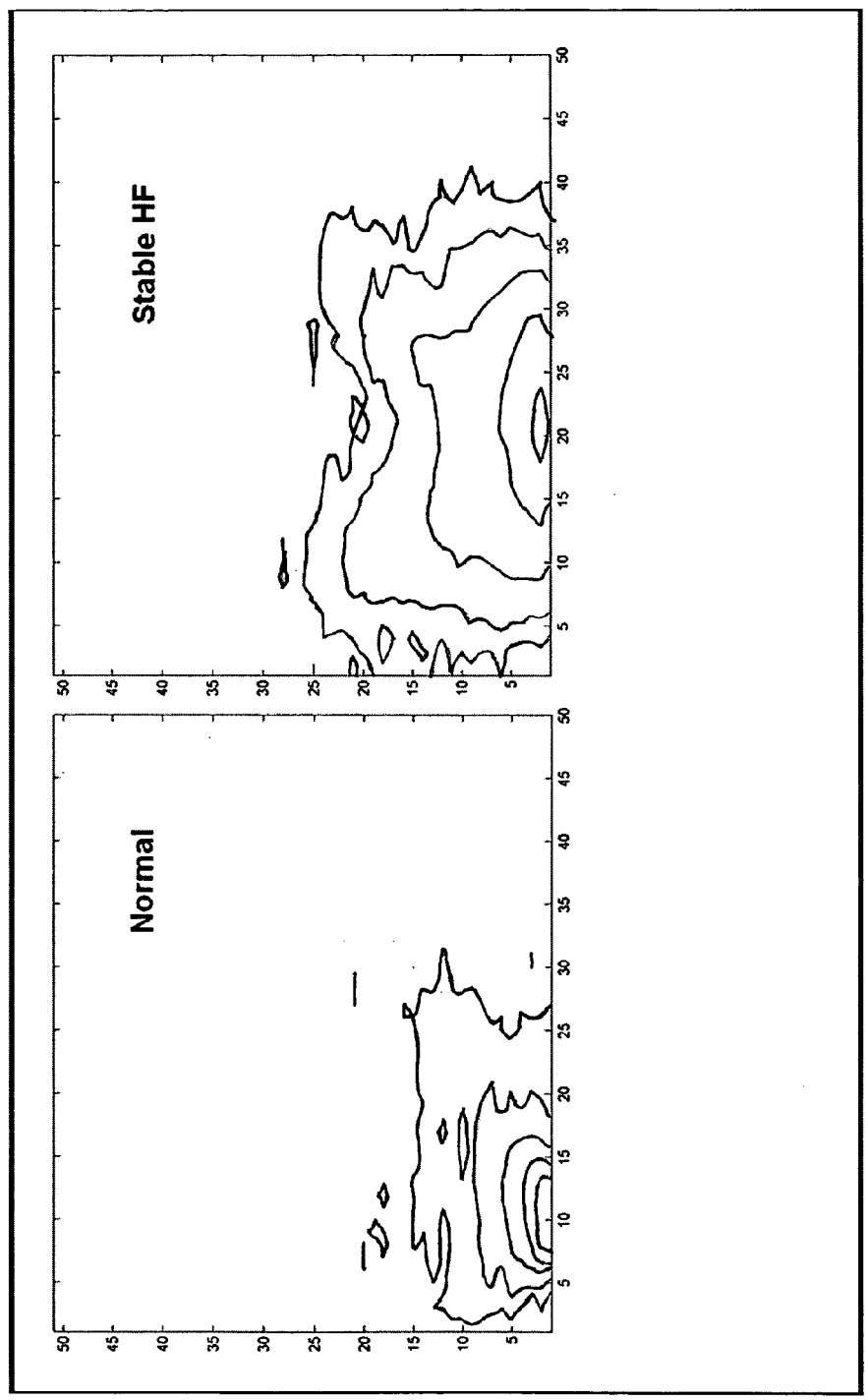
FIG. 1 shows a respiration rate variability footprint for a normal subject developed in accordance with embodiments of the present invention.
FIG. 2 shows an RRV footprint for a stable heart failure patient developed in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following discussion of various illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A medical device or system according to the present invention may include one or more of the features, structures, methods, or combinations thereof described hereinbelow. For example, patient-external and implantable devices may be implemented to include one or more of the advantageous features and/or processes described below. It is intended that such a device need not include all of the features described herein, but may be implemented to include selected features that provide for useful structures and/or functionality. Such a device may be implemented to provide a variety of therapeutic or diagnostic functions.

A wide variety of implantable medical devices, such as cardiac sensing and/or stimulation devices, may be configured to implement a respiration parameter variability detection and footprint generation methodology of the present invention. A non-limiting, representative list of such devices includes cardiac monitors, pacemakers, cardiovertors, defibrillators, resynchronizers, and other cardiac sensing and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Such devices are referred to herein generally as a patient-implantable medical device (PIMD) for convenience.

The present invention is directed to systems and methods for detecting respiration disturbances and changes in respiration disturbances, preferably by detecting variability in one or more respiration parameters. The present invention is further directed to determining respiration rate variability or RRV for a variety of diagnostic and therapeutic purposes, including disease/disorder detection, diagnosis, treatment, and therapy titration/optimization, for example. The present invention is also directed to systems and methods of generating a footprint, such as a two- or three-dimensional histogram, representative of a patient's respiration parameter variability (e.g., respiration rate variability), and generating one or more indices representative of quantitative measurements of the footprint.

The present invention is further directed to systems and methods that detect variability in one or more respiration parameters and heart rate variability (HRV). RRV detection can be combined with HRV detection to increase robustness of cardio-respiratory function assessment, particularly for patients having heart and respiration rates that fall within ranges associated with heart failure and decompensation (e.g., heart rates ranging from about 40 to 120 bpm and respiration rates ranging from about 10 to 30 breaths per minute). An RRV footprint may be combined with an HRV footprint to measure and track a patient's cardio-respiratory function.

Respiration and parameters associated with respiration, such as rate and tidal volume, can be used to detect and monitor conditions, such as heart failure status, periodic breathing (e.g., Cheyne-Stokes Respiration), sleep disordered breathing, such as apnea or hypopnea, and other forms of disordered breathing, such as dyspnea. Respiratory information can be obtained using one or more sensors. The sensors may be configured as implantable sensor or patient-external sensors. A combination of implantable and patient-external sensors may be used.

Respiration-modulated signals may be obtained using a variety of sensors, including a respiratory band (e.g., elastic bands) sensing arrangement, a minute ventilation sensor, impedance sensor, accelerometer, pressure sensor, cardiac sensors (e.g., ECG sensor), electromyogram (EMG) sensor, and/or air flow sensor such as that of a positive airway pressure device (e.g., continuous positive airway pressure device) or a ventilator, for example.

In addition to the sensors listed above, embodiments of the present invention may use one or more sensors for sensing any of a number of different physiological signals that are modulated by patient respiration. Suitable signals include respiration-modulated cardiac electrical signals and respiration-modulated mechanical signals. By way of example, suitable signals include ECG signals (surface, intrathoracic, or subcutaneous non-intrathoracic), R-R intervals (e.g., peak R modulation), P-R intervals, other conduction intervals, QRS vector shifts as a function of respiration, systolic time interval (STI), pulse transit time (PTT), blood pressure, intrathoracic pressure, plural pressure, left ventricular transmural pressure, transthoracic impedance, intra-cardiac pressures, minute ventilation, pulse oximetery signals, plethysmography signals, signals indicative of diaphragmatic movement, heart movement or acceleration due to lung movement, heart sounds, among other physiological signals that may be used as a surrogate for respiration. Further examples of sensors and techniques for developing a suitable respiration signal are disclosed in commonly-owned U.S. patent application Ser. Nos. 10/309,770 filed Dec. 4, 2002 and 10/930,979 filed Aug. 31, 2004, and in U.S. Pat. No. 6,076,015, which are hereby incorporated herein by reference.

In broad and general terms, a footprint (e.g., multi-dimensional histogram) may be generated using respiratory information acquired during a predefined time window, such as 24 hours, or during certain physiological states, such as exercise, sleep, or wakefulness. One or more indices are generated as quantitative measurements of the footprint. The footprint and its indices may be used for a variety of diagnostic and therapeutic purposes.

According to various embodiments, a respiration-modulated signal is obtained using a respiration sensor and variability of a respiration parameter is computed using the respiration-modulated signal. Respiration parameter variability is computed as the differences in the respiration parameter between adjacent breaths. For example, the respiration parameter may be respiration rate (RR) and the respiration parameter variability may be respiration rate variability (ΔRR) computed as the difference in RR between adjacent breaths. A footprint or multi-dimensional histogram may be developed based on the respiration parameter (e.g., RR) and variability of the respiration parameter (e.g., ΔRR), and one or more indices may be generated as quantitative measurements of the footprint.

The footprint contains a general pattern that indicates the patient's overall respiration variability. A third dimension may be added to, or superimposed on, the footprint. The third dimension may be indicated by use of a color code/scheme or by graphical indicia extending from a two-dimensional plane of the footprint into a plane orthogonal of this two-dimensional plane (e.g., cones, hills, valleys, etc.). The third dimension may be representative of tidal volume, a duration of time in which the patient is in a particular respiration pattern or a frequency of occurrence of a particular respiration pattern or rate, for example.

Useful footprint indices include a feature of the footprint, a pattern of the footprint, an area of the footprint, a location of the footprint, a shape of the footprint, and a contour of the footprint. Other useful footprint indices include ectopic islands of the footprint and a conditional distribution developed from the footprint (e.g., respiration rate histogram or respiration rate variability histogram). Still other useful footprint indices include a mapping of the footprint to one or more patient states. Examples of such patient states include patient activity, time of day, a sleep state, and wakefulness.

By way of example, an increase in the area of an RRV footprint indicates a worsening of a patient's heart failure status. The location of the RRV footprint (which is a surrogate to median/mean daily RR) indicates RR changes (higher and lower) and the worsening or improvement of a patient's heart failure status. Shape and contour of the RRV footprint are indicative of respiration patterns. A relatively smooth and confined shape/contour is indicative of stable HF status. An irregular shape/contour (e.g., horns, ears) is indicative of an acute HF status. Ectopic islands may be associated with different respiration patterns, such as Cheyne-Stokes Respiration, arising as isolated patterns at disparate locations.

Detecting variability in a respiration parameter and generating a footprint of same with associated indices may be used to quantitatively assess a patient's HF status or disordered breathing status. The footprint and associated indices may be used to initiate, adjust or terminate therapy delivery to the patient (via manual or automatic means), or to indicate need for interventional action by the patient or clinician (e.g., an alert/alarm or call to physician), among other uses.

Therapies delivered to the patient may include drug therapies, such as diuretics, dosages of which may be adjusted. Other therapies may involve cardiac stimulation therapy, such as by use of a cardiac resynchronizer device, that increases the patient's heart rate a modest amount, for example 5 to 10 beats per minute, to adapt the heart rate to the patient's need for oxygen. Further therapies may involve respiration therapies, such as therapies delivered via a continuous positive airway pressure (CPAP) device, which may also provide for pharmacological agent delivery via the CPAP device. It is noted that a CPAP, other type of positive airway pressure device or ventilator, or elastic respiratory band arrangement as is known in the art may be used to detect patient respiration in accordance with the principles of the present invention. Examples of useful respiration detection techniques and disordered breathing therapies are disclosed in commonly-owned U.S. patent application Ser. No. 10/309,770 filed Dec. 4, 2002 and Ser. No. 10/930,979 filed Aug. 31, 2004, which are hereby incorporated herein by reference.

Embodiments of the invention are directed to monitoring aspects of respiration using patient-implantable or patient-external sensing for monitoring the status of HF patients. A primary benefit of such monitoring is the identification and possible prediction/prevention of heart failure decompensation episodes. A patient-implantable sensing capability according to the present invention may be viewed as an "early warning system" for heart failure decompensation, utilization of which may lead to reduced hospitalization, improved quality of life, and possibly reduced mortality for HF patients with implanted devices. Because of the potential for directly measuring signs associated with disordered breathing, such as dyspnea, monitoring of respiration parameter variability and footprint generation in accordance with the present invention provides valuable data for clinicians managing heart failure patients.

FIGS. 1-6B are illustrations of RRV footprints developed in accordance with the principles of the present invention. The RRV footprints shown in the figures are color coded indicative of a third-dimension added to the two-dimensional RRV footprint. Although contour lines in FIGS. 1-6B are preferably represented in different colors to indicate such third-dimension information, such coloring of contour lines is not shown in the black and white rendering of the application drawings. As discussed further below, the different colors indicate differences in the parameter that defines the third dimension.

A brief description of FIGS. 1-6B will now be provided. FIG. 1 shows an RRV footprint for a normal subject. The RRV footprint is centered around 10 breaths per minute (br/m) and the contour is confined and smooth. FIG. 2 shows an RRV footprint for a stable HF patient. The RRV footprint in FIG. 2, as compared to that of FIG. 1, is shifted to the right, indicative of a higher RR, has both wider range of RR and ΔRR, and a contour that is still relatively smooth. It can be seen that the area of the RRV footprint for the stable HF patient in FIG. 2 is markedly greater than that of the RRV footprint for the normal subject shown in FIG. 1. RRV footprints that show increased area and movement to the right (e.g., higher RR) are generally indicative of a worsening heart failure status.

Figure 3:
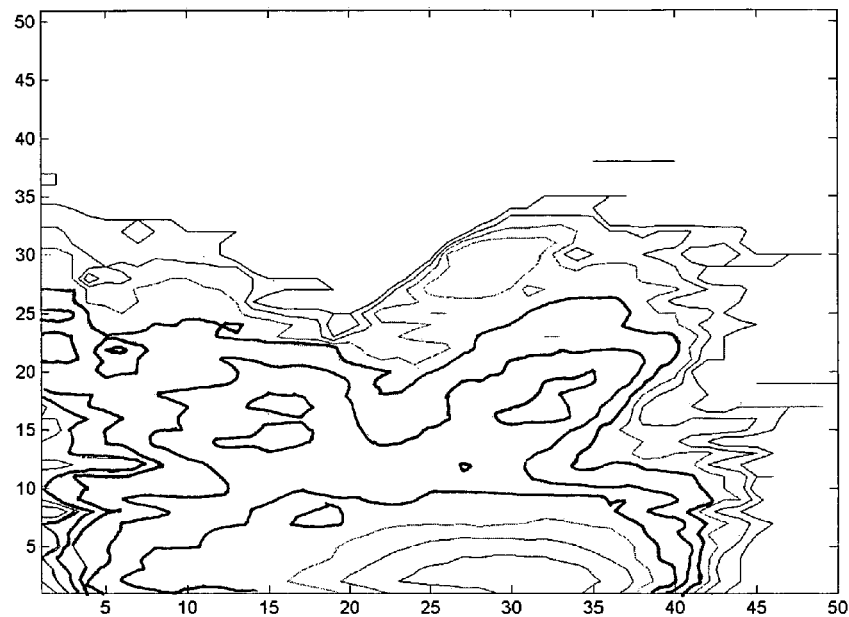
FIG. 3 shows an RRV footprint for a hospitalized HF patient at admission developed in accordance with embodiments of the present invention.
Figure 4:
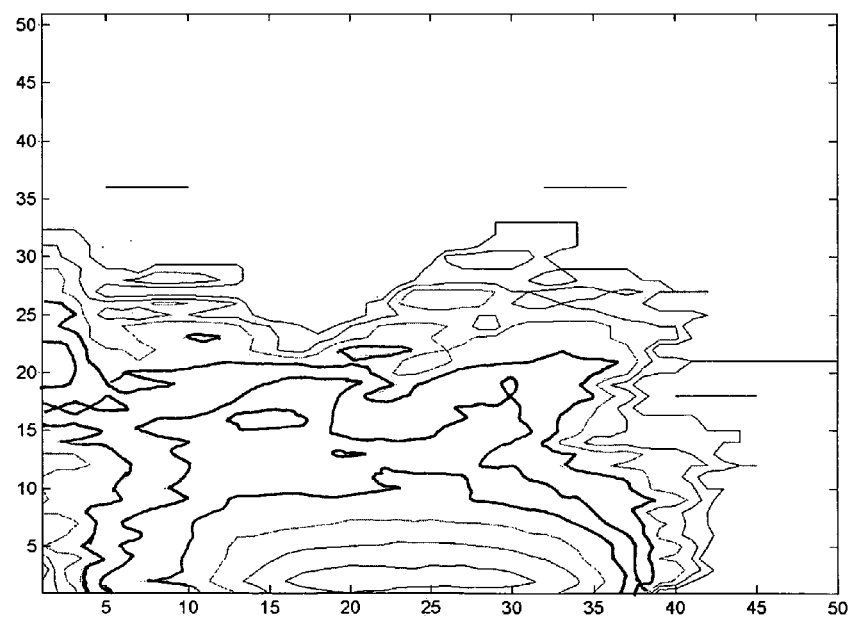
FIG. 4 shows an RRV footprint for the same HF patient of FIG. 3 at discharge developed in accordance with embodiments of the present invention.

FIG. 3 shows an RRV footprint for a hospitalized HF patient at admission. FIG. 4 shows an RRV footprint for the same HF patient at discharge, and indicates an improved HF status of the patient. The RRV footprint for the patient at admission shown in FIG. 3 is significantly drifted to the right, has a large footprint area with extremely irregular contour, and many isolated islands indicative of abnormal breathing patterns, periodic breathing in this case. The patient's RRV footprint at discharge; shown in FIG. 4, is less shifted to the right than in FIG. 3, and has a large footprint but with limited isolated islands, indicating an improvement in periodic breathing.

Figures 5A, 5B:
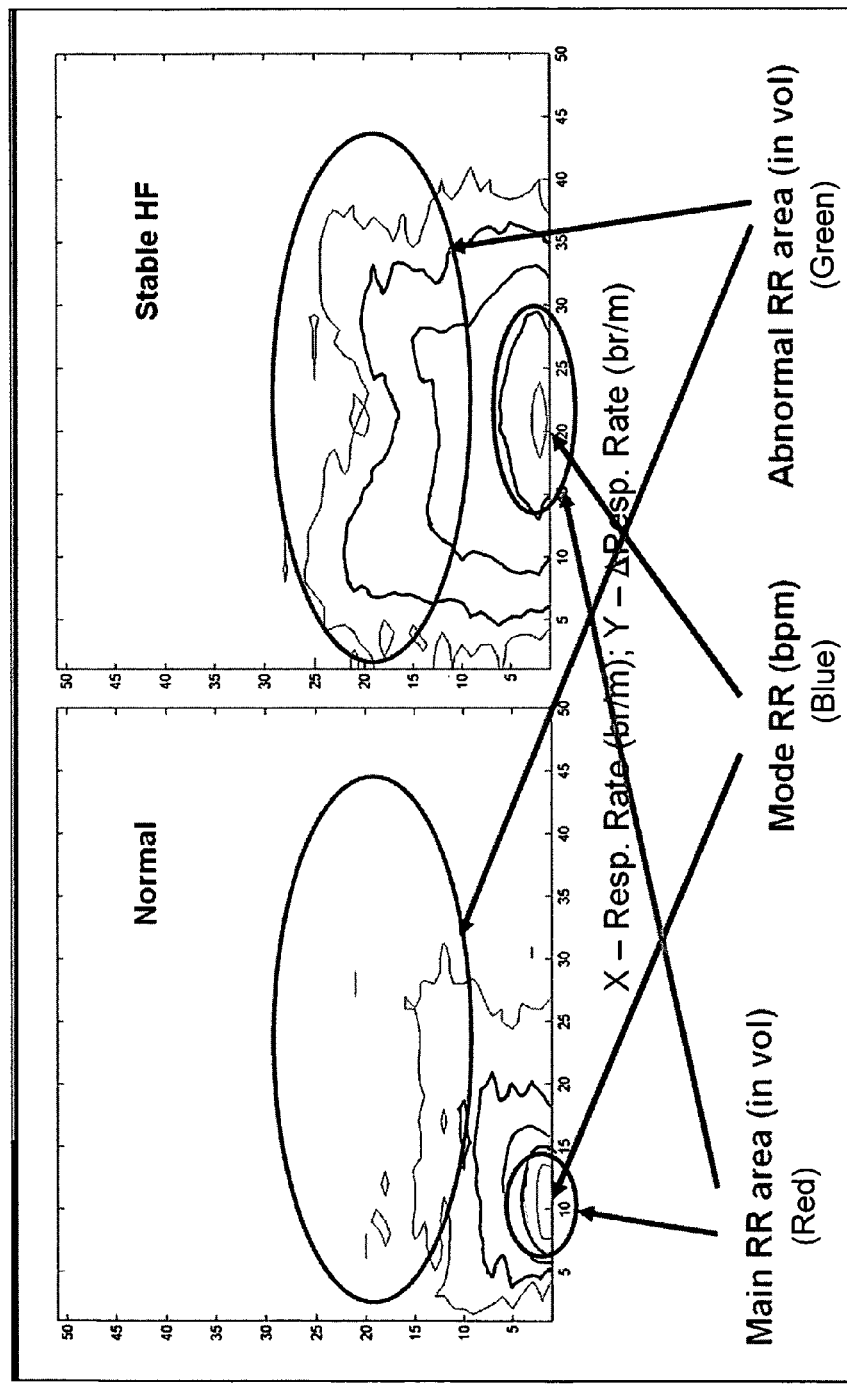
FIGS. 5A and 5B show an RRV footprint for a normal patient (FIG. 5A) next to an RRV footprint for a stable HF patient (FIG. 5B) developed in accordance with embodiments of the present invention, with various regions of the footprints preferably colored and annotated to accentuate portions of the footprints of particular interest.

FIGS. 5A and 5B show an RRV footprint for a normal patient (FIG. 5A) next to an RRV footprint for a stable HF patient (FIG. 5B). In FIGS. 5A and 5B, various regions of the footprints are preferably colored, and annotation may be added (e.g., arrows, ovals, and corresponding descriptors) to accentuate portions of the footprints of particular interest. For example, different regions of the footprints may be colored with red (denoting the Main RR area in vol.), blue (denoting the Mode of RR in br/m), and green (denoting Abnormal RR area in vol.). Further, the contour lines shown in FIGS. 5A and 5B may be presented in different colors to represent a third dimension of information that may be added to, or superimposed on, the footprint. It is understood that FIGS. 5A and 5B of the application drawings lack the color attributes discussed above, but that such colorization is preferably employed to enhance an understanding of the information and features presented in the RRV footprints.

In this illustrative example, the different colors of the contour lines in FIGS. 5A and 5B correspond to a different frequency of occurrence, with red representing highest occurrence and green lowest occurrence. FIGS. 5A and 5B show differences in each color-encircled region depending on the HF status of the patient. Such differences include the location, area, and/or shape of each color-encircled region. For example, the RRV footprint for the stable HF patient in FIG. 5B shows a significant shift to the right in the mode of RR (blue arrow point) and significant enlargement of both the main RR area (red circled region) and abnormal RR area (green circled region) relative to the RRV footprint for a normal patient shown in FIG. 5A. The magnitude of differences between the two footprints is reflective of a change in the HF status of the patient.

Figures 6A, 6B:
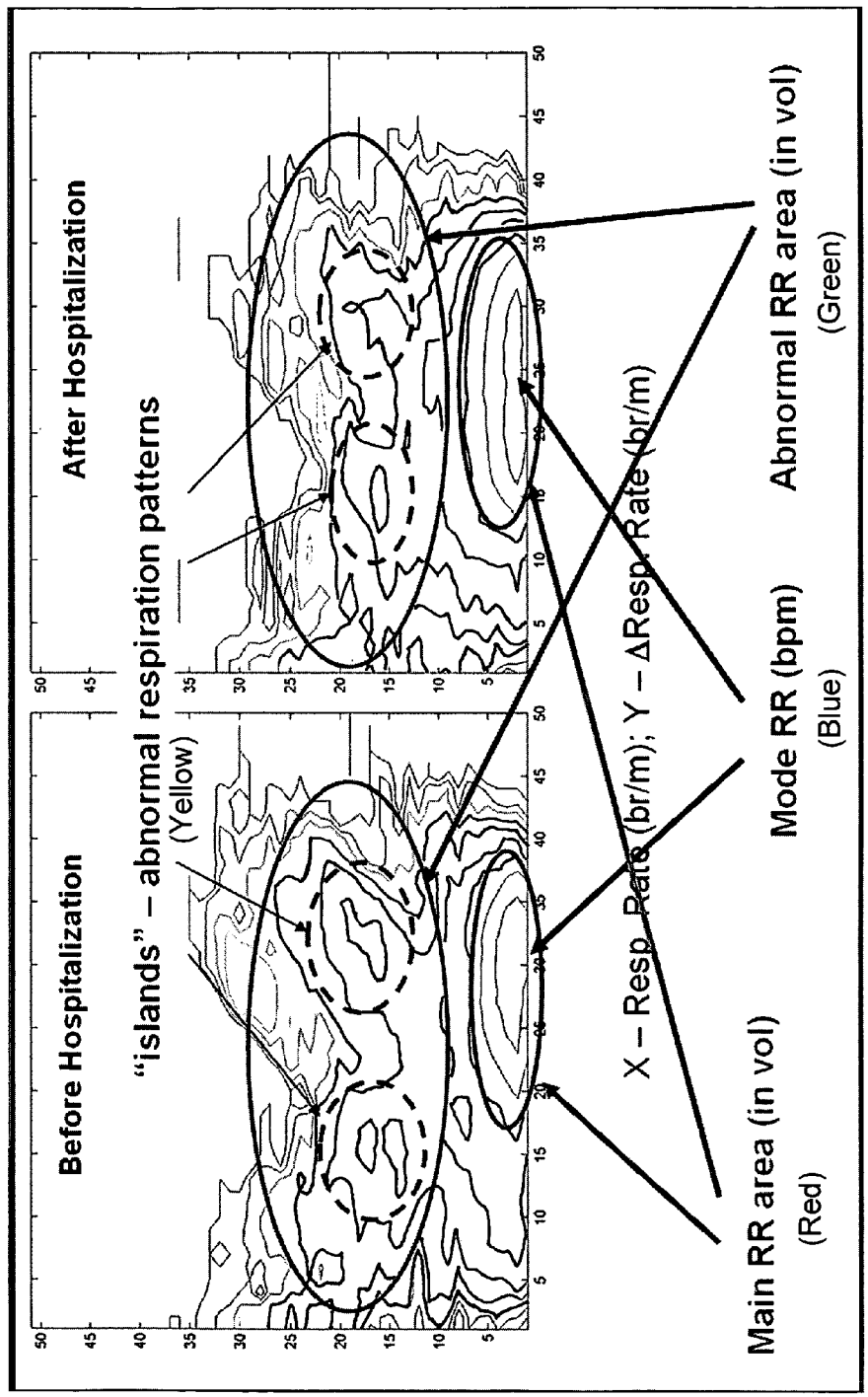
FIGS. 6A and 6B show RRV footprints developed in accordance with embodiments of the present invention for the same HF patient before and after hospitalization, with FIG. 6B evidencing general improvement in the patient's HF status after hospitalization.

FIGS. 6A and 6B show RRV footprints for the same HF patient before and after hospitalization. FIG. 6B evidences general improvement in the patient's HF status after hospitalization. Of particular interest are the ectopic "islands" highlighted as yellow regions denoted by dashed ovals in FIGS. 6A and 6B. These islands are associated with abnormal respiration patterns, such as Cheyne-Stokes Respiration. The RRV footprint of FIG. 6B developed after patient hospitalization shows a reduction of the island areas, indicating a reduction in Cheyne-Stokes Respiration, for example.

Figure 7:
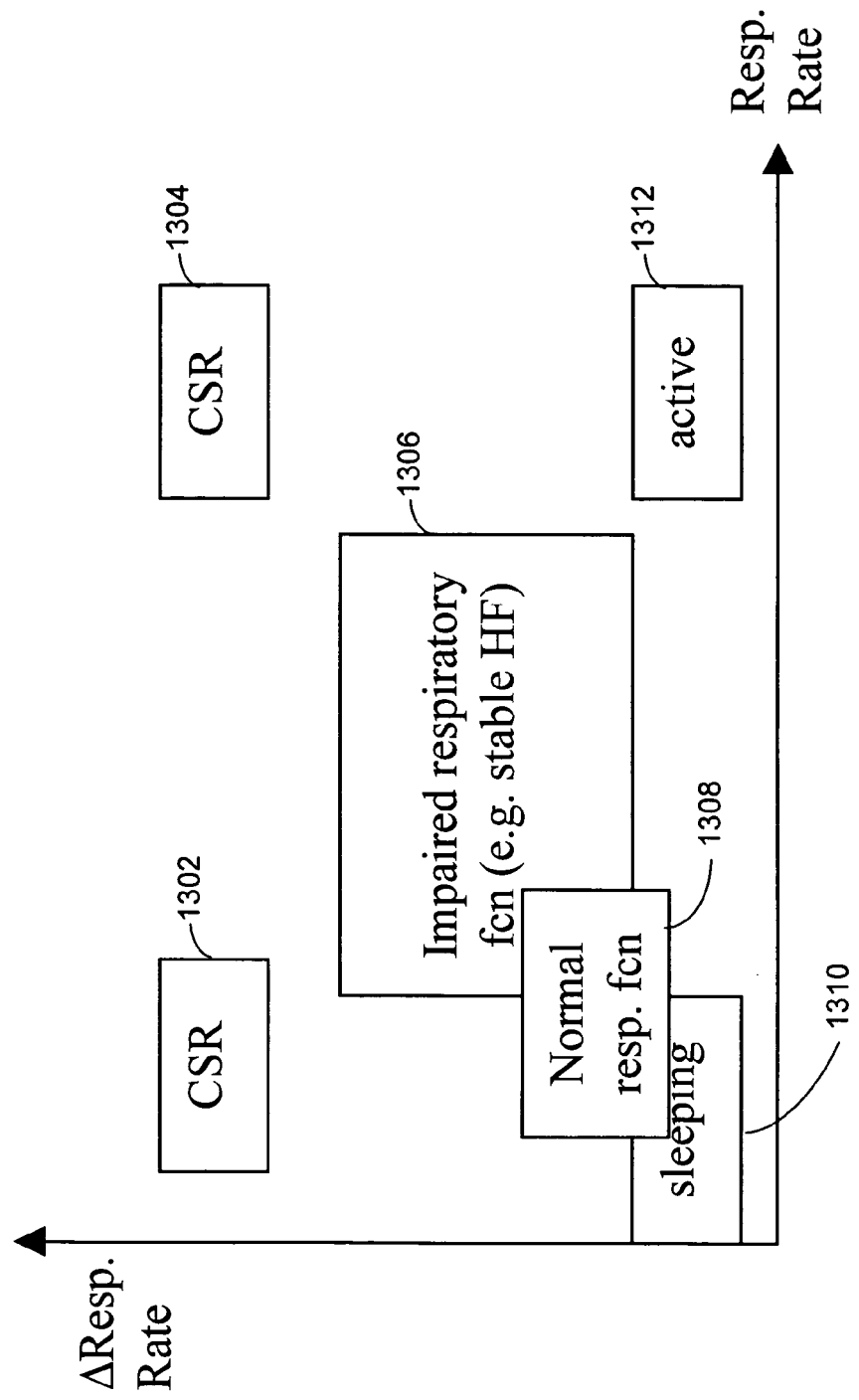
FIG. 7 illustrates regions of interest associated with an RRV footprint map developed in accordance with the present invention.

FIG. 7 is a mapping of regions of interest associated with an RRV footprint developed in accordance with the present invention. These regions represent characterizations of patient status or condition based on a clinical appreciation of how RRV footprint characteristics correspond with patient status or condition. For example, the presence of islands within regions 1302 and 1304 indicates the presence of Cheyne-Stokes Respiration. An increase in footprint area within region 1306 indicates an increase in impaired respiratory function (e.g., stable HF). An increase in footprint area within region 1308 indicates an increase in normal respiratory function. An increase in footprint area within region 1310 is an indication of patient sleep, while an increase in footprint area within region 1312 is an indication of increased patient activity. FIG. 7 provides a generalized "guide" to interpreting an RRV footprint. Regions, patterns, features, and other aspects of an RRV footprint may be visually (manually) or algorithmically analyzed based on such a guide or map to facilitate manual or automatic interpretation and quantification of an RRV footprint.

Figure 8:
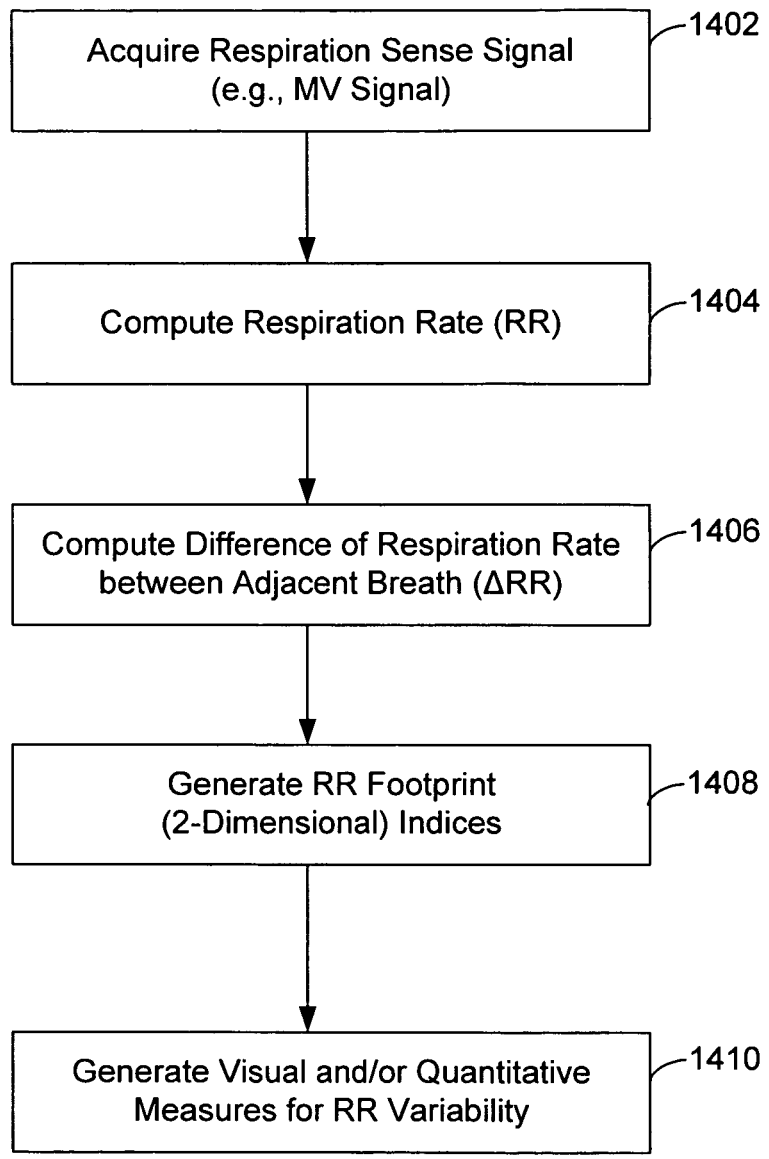
FIG. 8 is a flow diagram of a method for determining respiration rate variability and generating a footprint of same with associated indices in accordance with embodiments of the present invention.

Turning now to FIG. 8, there is shown a flow diagram of a method for determining respiration rate variability and generating a footprint of same with associated indices in accordance with embodiments of the present invention. A respiration sense signal is obtained 1402 and a respiration rate, RR, is computed 1404 using the respiration sense signal. A difference of respiration rate, $\Delta RR$, between adjacent breaths is computed 1406. An RR footprint is generated and indices are generated 1408 from the footprint. Visual and/or quantitative measures for respiration rate variability are generated 1410.

Figure 9:
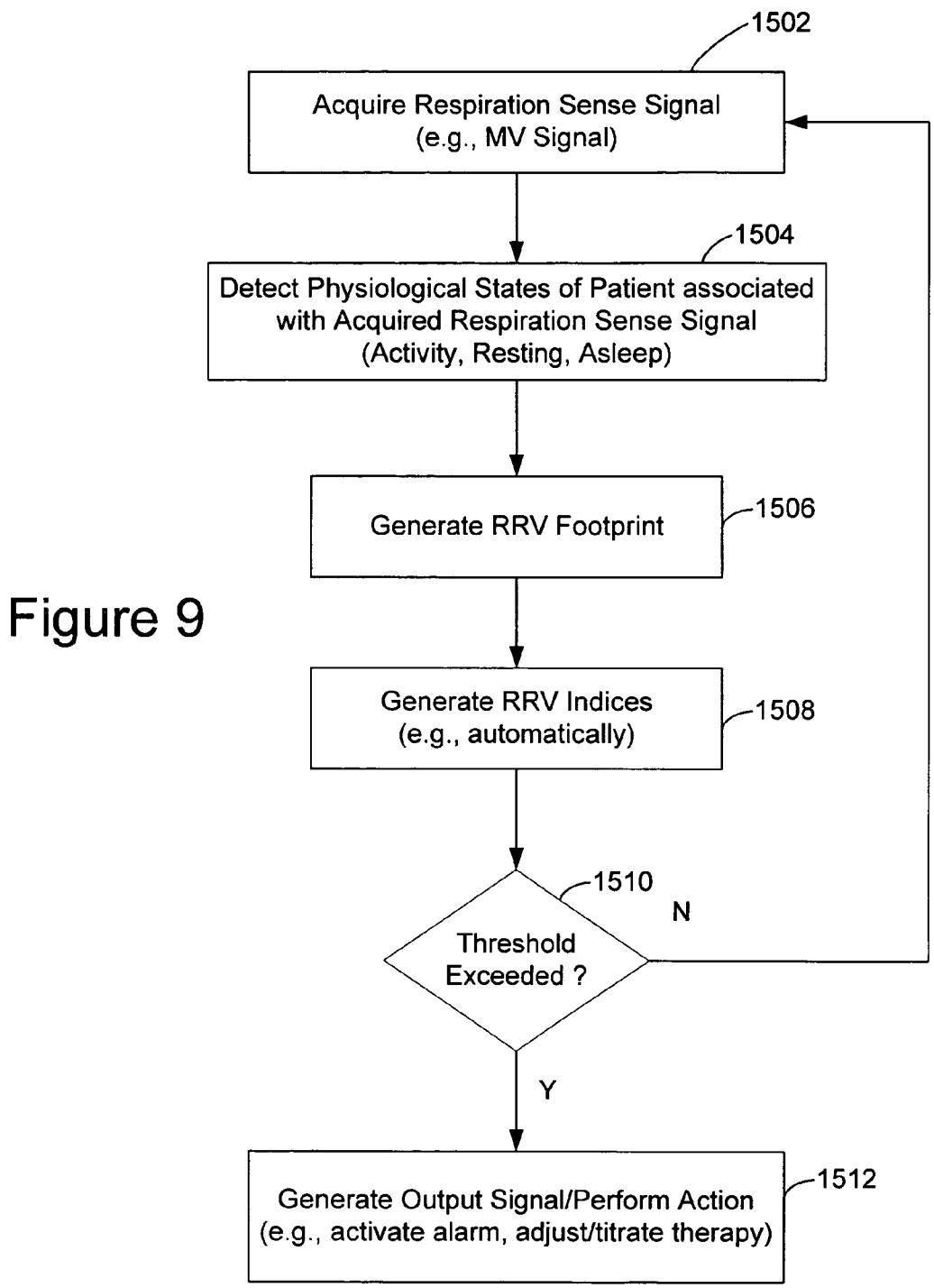
FIG. 9 is a flow diagram of a method for determining respiration rate variability and generating a footprint of same with associated indices in accordance with other embodiments of the present invention.

FIG. 9 is a flow diagram of a method for determining respiration rate variability and generating a footprint of same with associated indices in accordance with other embodiments of the present invention. A respiration sense signal is obtained 1502, such as from a minute ventilation sensor. Physiological states of the patient associated with the respiration sense signal are detected 1504. An RRV footprint is generated 1506 and RRV indices are generated 1508, preferably automatically or algorithmically. Upon exceeding a threshold, 1510, an output, such as an alarm, is generated 1512 or some interventional action is performed, such as adjustment or titration of a therapy delivered to the patient.

Figure 10:
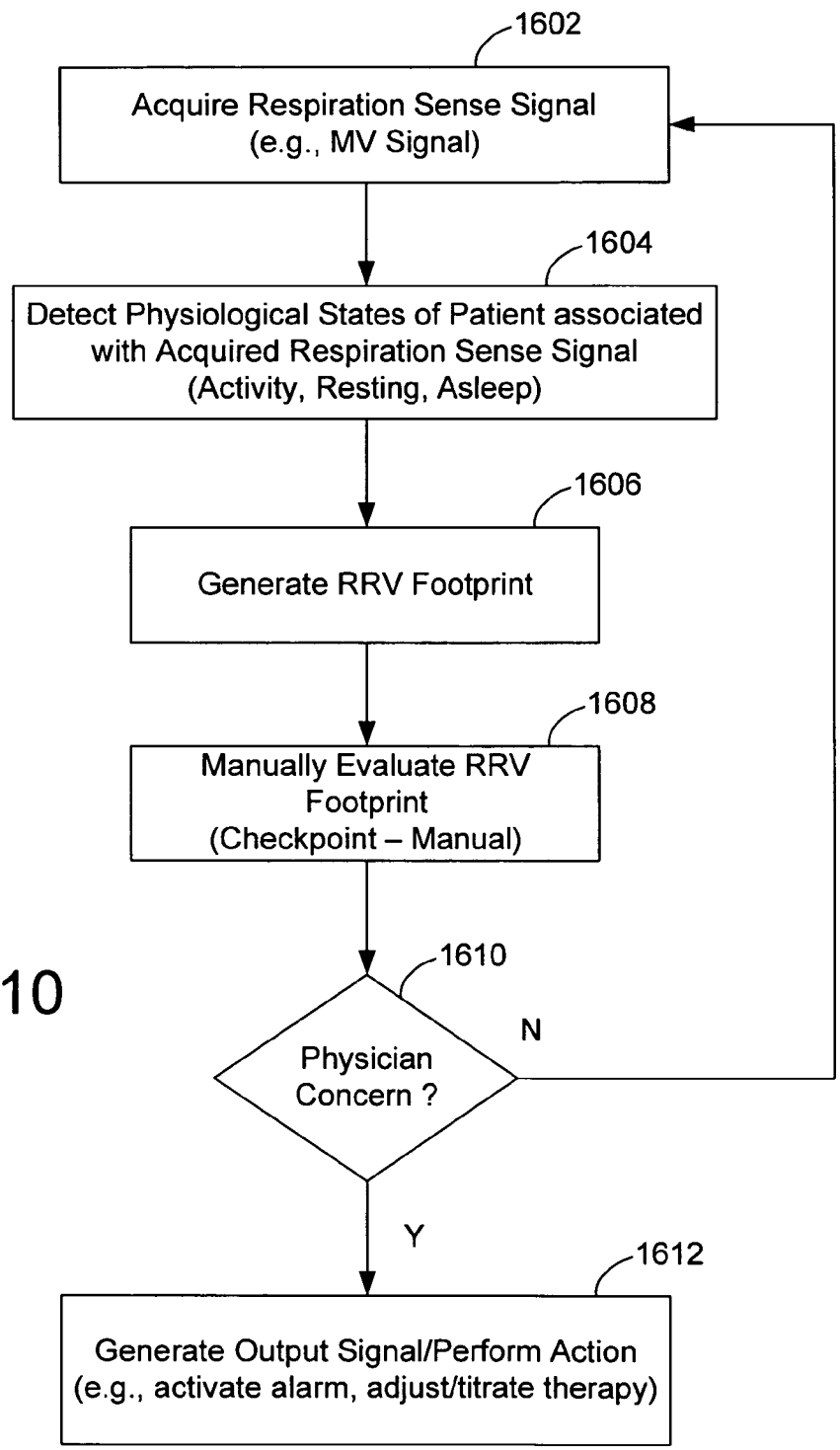
FIG. 10 is a flow diagram of a method for determining respiration rate variability and generating a footprint of same with associated indices in accordance with further embodiments of the present invention.

FIG. 10 is a flow diagram of a method for determining respiration rate variability and generating a footprint of same with associated indices in accordance with further embodiments of the present invention. A respiration sense signal is obtained 1602, such as from a minute ventilation sensor. Physiological states of the patient associated with the respiration sense signal are detected 1604. An RRV footprint is generated 1606. The RRV footprint is evaluated 1608 manually, such as by a physician, typically using a display or plot of the RRV footprint presented via a graphical user interface (GUI). The physician, rather than a processor as in the embodiment of FIG. 9, may selectively cause the generation of various RRV indices of interest by a processor via the GUI. Based on the manual evaluation, the physician may initiate generation 1612 of an output, such as an alarm, or some interventional action, such as adjustment or titration of a therapy delivered to the patient.

Figure 11:
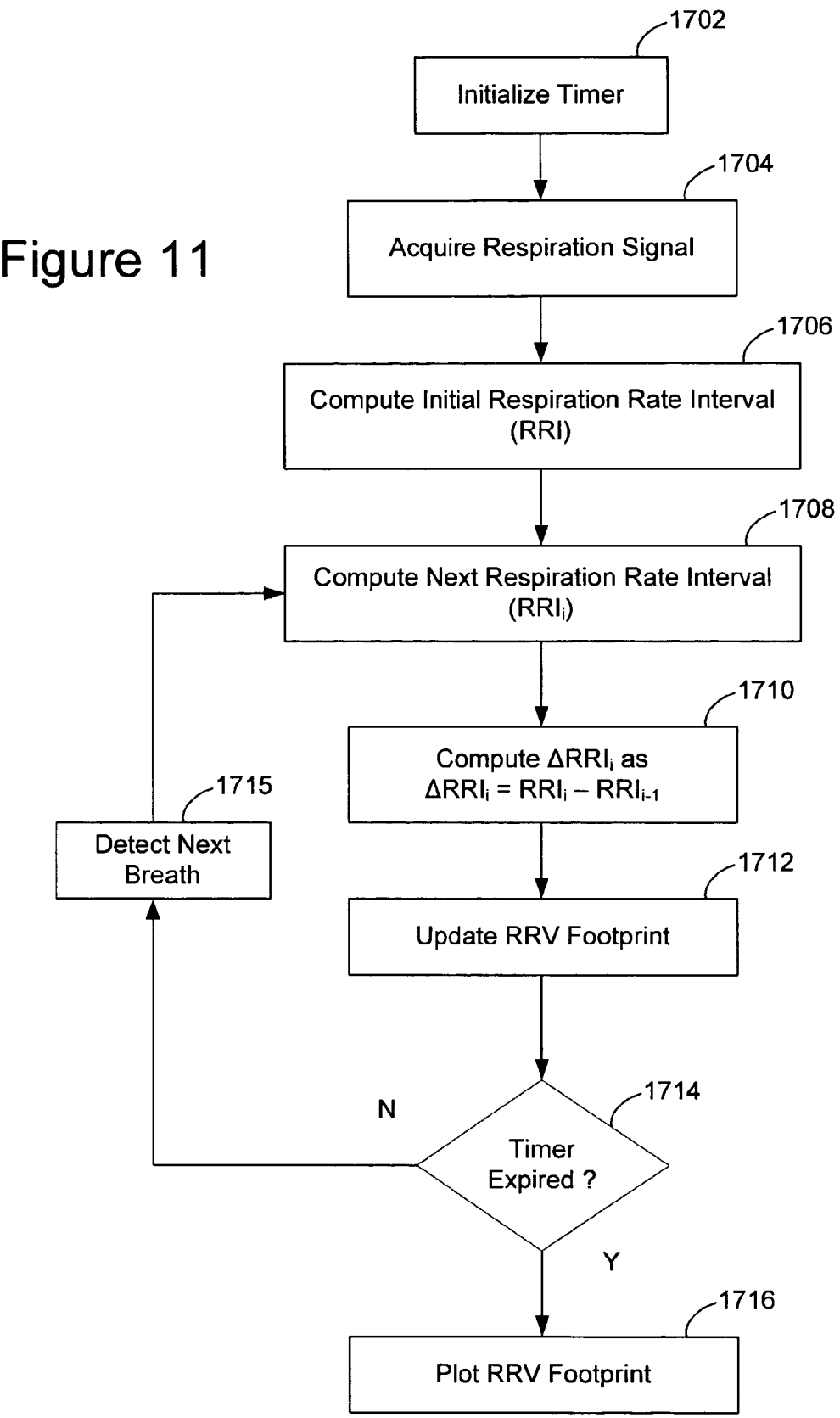
FIG. 11 is a flow diagram of a method for generating an RRV footprint in accordance with an embodiment of the present invention.

FIG. 11 is a flow diagram of a method for generating an RRV footprint in accordance with an embodiment of the present invention. A timer is initialized 1702, which preferably defines the beginning of a predefined time window, such as 24 hours, for example. A respiration signal is obtained 1704 and an initial respiration rate interval (RRI) is computed 1706. The next RRI ($RRI_i$) is computed 1708 using the respiration signal. A difference between the two adjacent RRIs is computed 1710 as $\Delta RRI_i = RRI_i - RRI_{i-1}$. An RRV footprint is updated using the computed value of $\Delta RRI_i$ 1712 and a check is made to determine 1714 if the timer has expired. If not, the next breath is detected 1715 and steps 1708-1714 are repeated. If the timer has expired, a plot of the RRV footprint may be generated 1716.

It is noted that patient breaths may be detected using a variety of techniques. For example, a respiration-modulated signal may be filtered and processed with a software zero-crossing breath detection algorithm with hysteresis, such as in accordance with the approach disclosed in commoniy-owned U.S. Pat. No. 6,076,015, which is hereby incorporated herein by reference. Detected patient breaths may be further analyzed to determine if such breaths qualify as valid breaths. A valid breath may be determined based on various respiration signal characteristics, such as amplitude and signal morphology, for example. Various known approaches may be employed to discern valid breaths that qualify for inclusion in subsequent processes.

Figure 12:
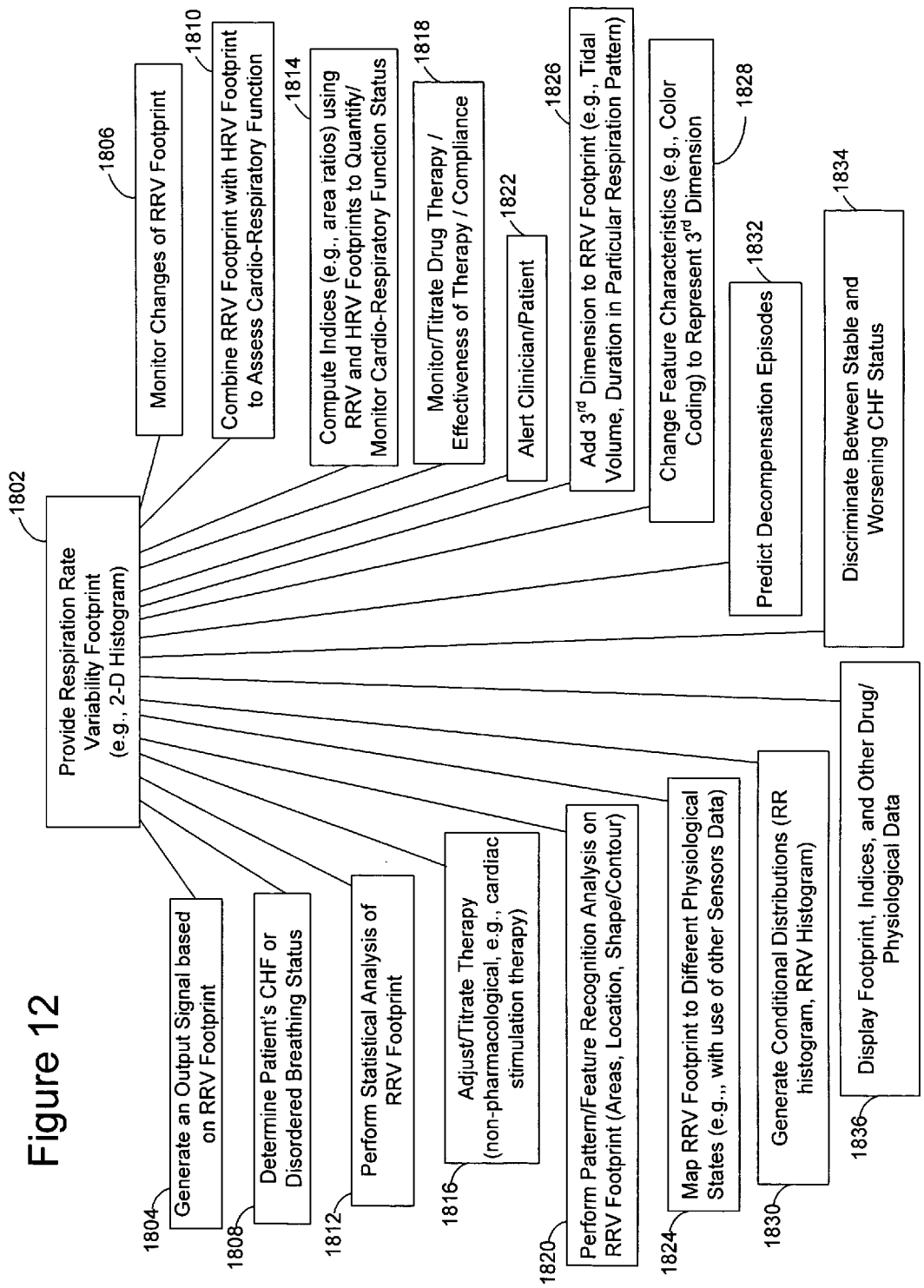
FIG. 12 is a block diagram showing a variety of illustrative operations that may be performed based on a respiration rate variability footprint with associated indices generated in accordance with the present invention.

FIG. 12 is a block diagram showing a variety of illustrative operations that may be performed based on a respiration rate variability footprint with associated indices 1802 generated in accordance with the present invention. As is shown in FIG. 12, a signal based on the RRV footprint may be generated 1804. The signal may take several forms, including an electrical or electromagnetic signal, optical signal, or acoustic signal, for example. This signal may be used for a variety of diagnostic and therapeutic purposes, including titration of a patient's drug regimen. The signal may be produced by a medical device implanted within the patient. The signal may also be produced by a patient-external device that receives respiration sensor data from a medical device implanted within the patient. Other output scenarios are contemplated.

Changes of the RRV footprint may be monitored 1806. HF status, change in HF status, disordered breathing status, and/or change is disordered breathing status may be determined 1808 and monitored. Various statistical analyses may be performed 1812 on the RRV footprint and associated indices may be computed. Drug, cardiac, respiration or other therapy may be monitored and titrated 1816 based on the RRV footprint and one or more indices. Effectiveness of the therapy may be quantified 1818 using the RRV footprint and associated indices. Patient compliance to a specified therapy regimen, such as a drug regimen, may also be monitored 1818. The patient and/or clinician may be prompted, such as by audible, textual, or visual means, as to the need for therapy or drug administration as originally prescribed or adjusted by the physician. Other types of therapies, such as cardiac or external respiration therapies (e.g., via a continuous positive airway pressure device), may be adjusted and titrated 1818. Patient compliance to a specified therapy may also be monitored.

An alert to the clinician and/or patient may be generated 1822 and communicated in various forms to the clinician and/or patient based on the RRV footprint and associated indices. The RRV footprint and associated indices may be used to predict decompensation episodes 1832. For example, gradual or sudden changes in an HF patient's respiration pattern can be detected from changes in the patient's RRV footprint and associated indices, which can indicate the relative likelihood of a decompensation episode. The RRV footprint and associated indices may be used to discriminate 1834 between stable and worsening HF status of a patient.

Pattern and/or feature recognition may be performed 1820 on the RRV footprint, such as for recognizing or identifying areas, locations, shapes/contours of interest that can be associated with particular respiration or patient conditions. Various known pattern and/or feature recognition techniques may be employed, such as by using neural networks and other statistical pattern recognition techniques. Such techniques may include principal component analysis, fisher and variance weight calculations and feature selection. Neural network methods may include a back propagation neural network and/or radial basis function neural network. Statistical pattern recognition may include linear discriminant analysis, quadratic discriminant analysis, regularized discriminant analysis, soft independent modeling of class analogy, and/or discriminant analysis with shrunken covariance.

An RRV footprint may be mapped 1824 to different physiological states, such as determined by other sensors (e.g., posture sensor, motion sensors). Conditional distributions may be generated 1830 from the RRV footprint. For example, a respiration rate (RR) histogram may be obtained by integrating the RRV footprint along the appropriate axis of the RRV footprint. A respiration rate variability histogram may be obtained by integrating the RRV footprint along the other axis of the RRV footprint.

An RRV footprint may be combined with an HRV footprint to provide increased robustness of cardio-respiratory function assessment. A combined RRV and HRV footprint provides for the measurement and tracking of a patient's cardio-respiratory function. Various indices, such as area ratios of the HRV footprint and RRV footprint, may be generated 1814 to quantify a patient's cardio-respiratory function status. Techniques for generating an HRV footprint of a type suitable for use in combination with an RRV footprint are disclosed in commonly-owned U.S. Pat. No. 6,026,320, which is hereby incorporated herein by reference. It is noted that an RRV footprint may also be generated in accordance with U.S. Pat. No. 6,026,320, as modified by the teachings of the subject disclosure to arrive at a useful RRV footprint.

A third dimension may be added to, or superimposed on, the footprint (e.g., two-dimensional histogram) 1826. Such third dimension may be tidal volume, a duration of time during which a patient is in a particular respiration pattern or a frequency of occurrence of a particular respiration pattern or rate, for example. The third dimension may be indicated 1828 by use of a color scheme or by a graphical construct or indicia extending from a two-dimensional plane of the footprint into a plane orthogonal of this two-dimensional plane.

A variety of RRV footprint and index data, trend data, and other drug and physiological data may be displayed 1836 for use by the patient, clinician, and/or physician. FIG. 12 is intended to provide a non-exhaustive, non-limiting listing of examples concerning the use of an RRV footprint developed using respiration rate data in accordance with the principles of the present invention.

Various embodiments described herein may be used in connection with devices that provide for HF monitoring, diagnosis, and/or therapy. A patient-implantable medical device or PIMD of the present invention may incorporate HF features involving dual-chamber or bi-ventricular pacing/therapy, cardiac resynchronization therapy, cardiac function optimization, or other HF related methodologies. For example, a PIMD of the present invention may incorporate features of one or more of the following references: commonly owned U.S. patent application Ser. No. 10/270,035, filed Oct. 11, 2002, entitled "Timing Cycles for Synchronized Multisite Cardiac Pacing;" and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of the present invention are disclosed in commonly owned U.S. Pat. Nos. 5,313,953; 5,388,578; and 5,411,031, which are hereby incorporated herein by reference.

Figure 13:
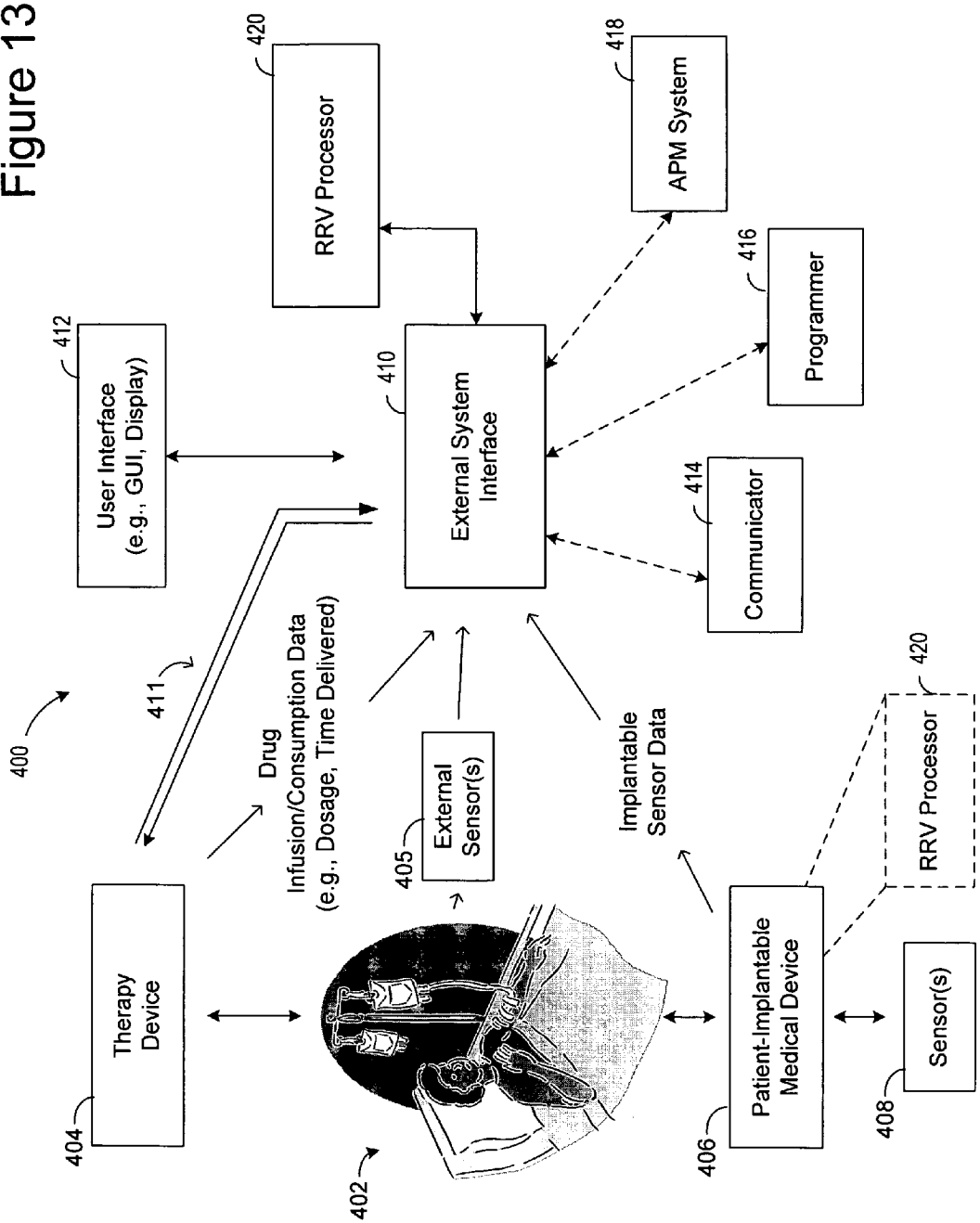
FIG. 13 is a block diagram of a system for managing patient care based on an RRV footprint and associated indices in accordance with the principles of the present invention.

Turning now to FIG. 13, there is shown a block diagram of a system 400 for managing patient care based on an RRV footprint and associated indices in accordance with the principles of the present invention. FIG. 13 shows a patient 402 that is receiving a therapy as prescribed by a physician. The therapy may be a drug therapy, a respiration therapy, a cardiac electrical therapy or other therapy. A drug therapy may be delivered to the patient 402 by infusion, for example, using a drug therapy device (e.g., drug pump device). The drug therapy may also be delivered by patient consumption of a prescribed medication(s), in which case the therapy device 404 may represent a pill counting device or drug consumption questionnaire, for example. A respiration therapy may be delivered to the patient 402 using a continuous positive airway pressure device or ventilator, for example. Cardiac therapy may be delivered using a patient-implantable medical device 406 or an external device. Combinations of therapies delivered to the patient 402 are also contemplated.

The system 400 shown in FIG. 13 includes a patient-implantable medical device 406 that is implanted in the patient 402. PIMD 402 incorporates or is coupled to one or more implantable sensors 408. One or more of the sensors 408 are configured to sense a respiration parameter of the patient's breathing. Such sensors 408 may include a minute ventilation sensor, transthoracic impedance sensor, accelerometer, or other sensor capable of producing a respiration waveform representative of the patient's breathing (see listing of respiration-modulated signals provided hereinabove that may be sensed using an appropriate sensor). A variety of external sensors 405 may also be used to sense various physiological parameters of the patient. Such external sensors 405 may include one or more of a pulse oximetry sensor, blood pressure sensor, patient temperature sensor, EKG sensor arrangement, among others.

The system 400 includes a number of patient-external devices. An external system interface 410 includes communication circuitry configured to effect communications with PIMD 406. External system interface 410 may also be configured to effect communications with the therapy device 404, such as by a unidirectional or bi-directional communication link. External system interface 410 may further be configured to effect communications with external sensors 405.

Uni-directional communications facilitates the transfer of therapy information (e.g., drug type, dosage, day/time of administration) from the therapy device 404 to the external system interface 410. It is understood that the external system interface 410 may be integral to, or separate from, the therapy device 404 in various embodiments. Bi-directional communications facilitates closed-loop management of the patient's therapy, which preferably allows for physician input/intervention within the loop established between the therapy device 404 and PIMD 406. This system configuration advantageously allows for automatic or semi-automatic titration of a therapy delivered to a patient.

The external system interface 410 may be communicatively coupled to, or integral with, one or more of a programmer 416, an advanced patient management system 418, a portable or hand-held communicator 414, or other patient-external system. The external system interface 410 is coupled to a user interface 412, such as a graphical user interface or other interface that provides a display. User interface 412 preferably includes a user actuatable input/output device, such as a keyboard, touch screen sensor, mouse, light pen, and the like. The user interface 412 may be used to input therapy information, such as type of drug(s) being administered, dosage of such drugs, times and dates of drug administration, patient information, including patient weight, perception of wellness, and other information relevant to the patient's condition, drug regimen or therapy.

An RRV processor 420 is shown coupled to the external system interface 410. Alternatively, RRV processor 420 may be incorporated as a component of the PIMD 406, as is shown in phantom. The RRV processor 420 may also be incorporated as a component of the communicator 414, programmer 416, or an advanced patient management (APM) system 418. The RRV processor 420 performs the various processes described above and generates an RRV footprint and indices developed from the RRV footprint. This and other relevant information is communicated to the external system interface 410 for display to the physician, clinician, and/or patient via the user interface 412, for example.

Figure 14:
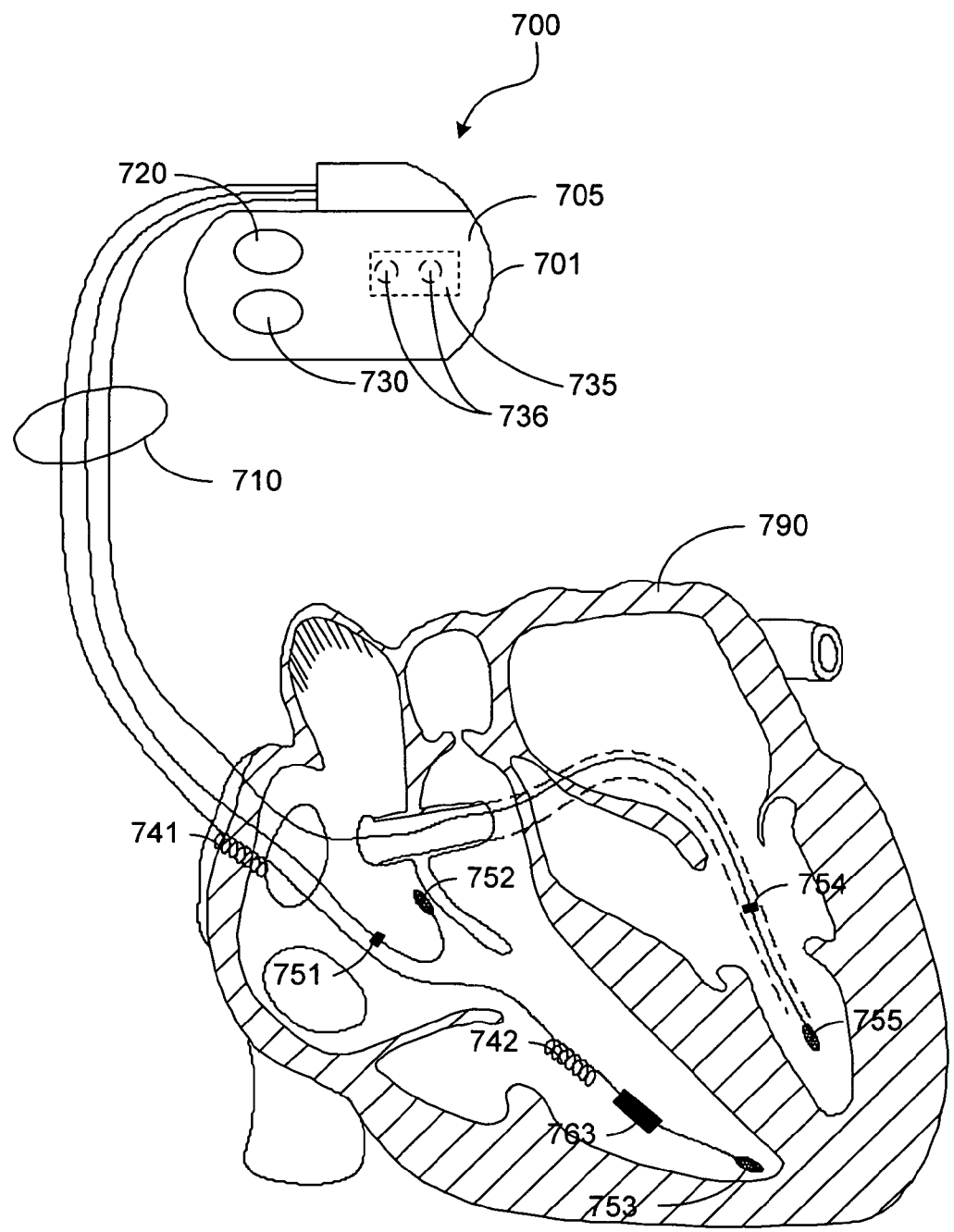
FIG. 14 is an embodiment of a patient-implantable medical device configured to sense one or more respiration parameters for purposes of determining a patient's respiration rate and respiration rate variability, from which an RRV footprint and associated indices may be generated in accordance with embodiments of the present invention.

Referring now to FIG. 14, there is illustrated an embodiment of a PIMD configured to sense one or more respiration parameters for purposes of determining a patient's respiration rate and respiration rate variability, from which an RRV footprint and associated indices may be generated in accordance with embodiments of the present invention. In this illustrative example, the PIMD includes a cardiac rhythm management device (CRM) 700 including an implantable pulse generator 705 electrically and physically coupled to an intracardiac lead system 710.

Portions of the intracardiac lead system 710 are shown inserted into the patient's heart 790. The intracardiac lead system 710 includes one or more electrodes and/or sensors configured to sense electrical cardiac activity of the heart, deliver electrical stimulation to the heart, sense the patient's transthoracic impedance, sense transthoracic total impedance, sense blood (internal filling) pressure, flow, and/or temperature, sense acceleration and/or body acoustics, and/or sense other physiological parameters of interest. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate a motion detector 720 that may be used to sense patient activity as well as various respiration and cardiac related conditions. For example, the motion detector 720 may be optionally configured to sense snoring, activity level, and/or chest wall movements associated with respiratory effort, for example. The motion detector 720 may be implemented as an accelerometer positioned in or on the housing 701 of the pulse generator 705. For a motion sensor implemented as an accelerometer, the motion sensor may also provide respiratory, e.g. rales, coughing, and cardiac, e.g. S1-S4 heart sounds, murmurs, and other acoustic information. An accelerometer may be used to develop respiration waveforms from which various respiration parameters may be developed.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 14, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 14 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and U.S. Patent Publication Ser. No. 2002/0143264, which are hereby incorporated herein by reference.

For purposes of illustration, and not of limitation, various embodiments of devices implemented in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. patent application Ser. No. 10/465,520 filed Jun. 19, 2003 and Ser. No. 10/738,608 filed Dec. 17, 2003, which are hereby incorporated herein by reference.

Figure 15:
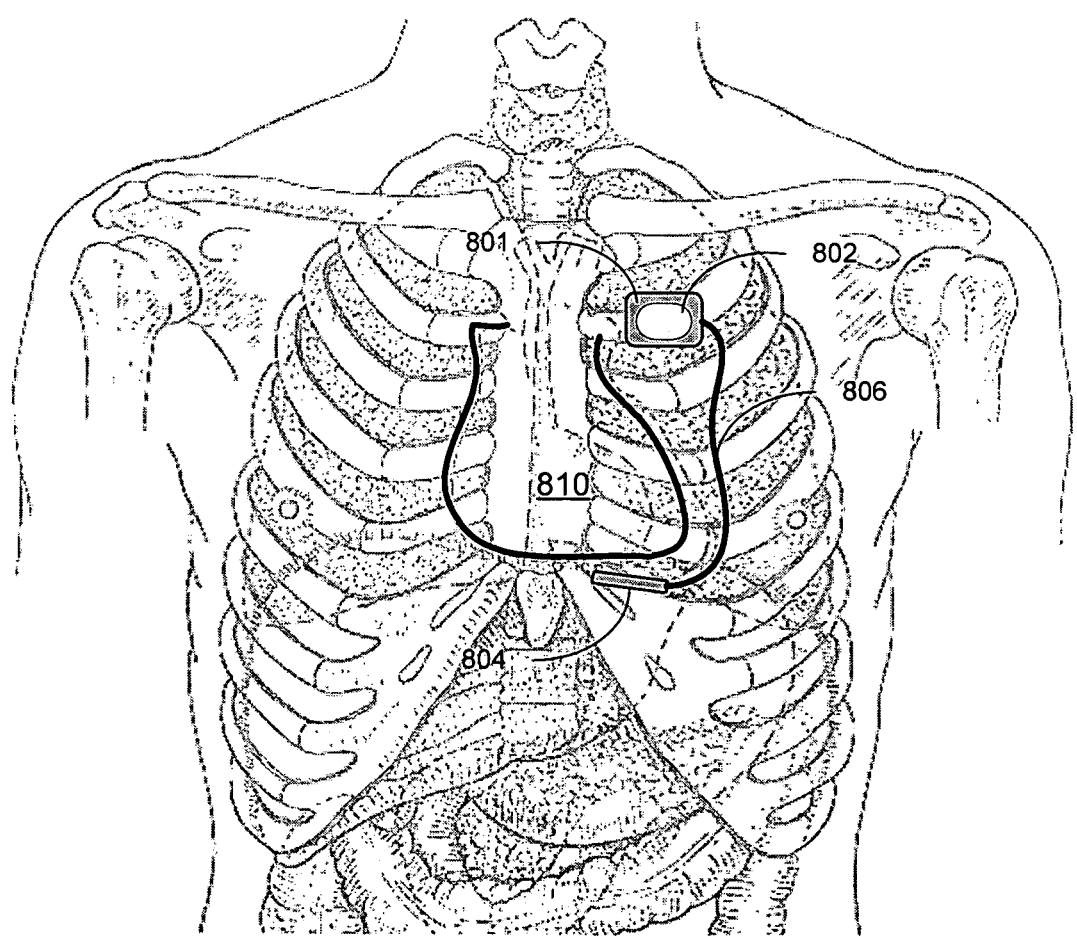
FIG. 15 is an embodiment of a subcutaneous, non-intrathoracic patient-implantable medical device configured to sense one or more respiration parameters for purposes of determining a patient's respiration rate and respiration rate variability, from which an RRV footprint and associated indices may be generated in accordance with embodiments of the present invention.

In one configuration, as is illustrated in FIG. 15, electrode subsystems of a PIMD system are arranged about a patient's heart 810. The PIMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the PIMD electronics. In one embodiment, the can electrode 802 includes the entirety of the external surface of housing 801. In other embodiments, various portions of the housing 801 may be electrically isolated from the can electrode 802 or from tissue. For example, the active area of the can electrode 802 may include all or a portion of either the anterior or posterior surface of the housing 801 to direct current flow in a manner advantageous for cardiac sensing and/or stimulation. For example, portions of the housing 801 may be covered with a non-conductive, or otherwise electrically resistive, material to direct current flow. Suitable non-conductive material coatings include those formed from silicone rubber, polyurethane, or parylene, for example.

The PIMD system shown in FIG. 15 incorporates one or more sensors configured to sense a parameter useful for detecting respiration. A sensor may be disposed on housing 801, such that element 802 may be representative of such sensor(s) alone or in combination with a can electrode. A sensor(s) may be disposed on another component of the PIMD system, such as on lead 806, a lead separate from lead 806, or on the subsystem element 804, which may be representative of such sensor(s) alone or in combination with a cardiac electrode.

A PIMD of the present invention may be implemented to communicate with a patient management server or network via an appropriate communications interface or an external programmer. A PIMD of the present invention may be used within the structure of an APM system. The advanced patient management system allows physicians to remotely and automatically monitor cardiac and respiratory functions, as well as other patient conditions.

In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a medical device for sensing one or more respiration parameters for purposes of determining a patient's respiration rate and respiration rate variability, from which an RRV footprint and associated indices may be generated in accordance with the present invention. It is understood that a wide variety of such medical devices are contemplated, ranging from relatively sophisticated to relatively simple designs. As such, particular external and implantable device configurations may include particular features as described herein, while other such device configurations may exclude particular features described herein.

Various modifications and additions can be made to the embodiments discussed hereinabove without departing from the scope of the present invention. It is understood that methods and systems of the present invention may be implemented using implantable and/or patient-external devices and sensors, and that the embodiments described herein may be implemented in the context of such implantable and/or patient-external devices and sensors. Accordingly, the scope of the present invention should not be limited by the particular embodiments described above, but should be defined only by the claims set forth below and equivalents thereof.

What is claimed is:

1. A system, comprising:
a medical device comprising sensing circuitry;
detection circuitry coupled to the sensing circuitry, the detection circuitry configured to detect a patient respiration parameter of a patient; and
a processor coupled to the detection circuitry, the processor configured to generate a footprint comprising a mapping of a plurality of contour lines representative of the patient's respiration parameter variability using a respiration-modulated signal detected by the detection circuitry, generate one or more indices as quantitative measurements of the footprint, wherein a first one of the one or more indices is representative of a size of the footprint, analyze the footprint using the one or more indices to identify one or more patterns indicative of disordered breathing, assess the patient's health status based on the analysis of the footprint to identify the one or more disordered breathing patterns, and generate an output based on the assessment of the patient's health status.

2. The system of claim 1, wherein the processor is configured to determine respiration rate based on the detected patient respiration parameter and the footprint is generated based on the patient's respiration rate variability.

3. The system of claim 1, wherein the sensing circuitry comprises a minute ventilation sensor.

4. The system of claim 1, wherein the processor is configured to determine tidal volume based on the detected patient respiration parameter and the footprint is based at least in part on the patient's tidal volume variability.

5. The system of claim 1, wherein the processor is further configured to map one or more portions of the footprint to a patient activity state.

6. The system of claim 1, wherein the one or more patterns indicative of disordered breathing comprise a feature of the footprint.

7. The system of claim 1, wherein the one or more patterns indicative of disordered breathing comprise an ectopic island of the footprint.

8. The system of claim 1, wherein the processor analysis of the footprint comprises identification of a location of the footprint that is indicative of disordered breathing.

9. The system of claim 1, wherein a second one of the one or more indices is representative of a shape of the footprint.

10. The system of claim 1, wherein the processor is further configured to map one or more portions of the footprint to one or both of patient sleep and wakefulness states.

11. The system of claim 1, wherein at least one of the one or more patterns indicative of disordered breathing is indicative of sleep disordered breathing.

12. The system of claim 1, wherein at least one of the one or more patterns indicative of disordered breathing is indicative of dyspnea.

13. The system of claim 1, wherein the processor assessment of the patient's health status comprises discrimination between stable and worsening heart failure status.

14. The system of claim 1, wherein the processor is further configured to map one or more portions of the footprint to time of day.

15. The system of claim 1, wherein the processor is further configured to map one or more portions of the footprint to patient posture.

16. The system of claim 1, further comprising a display device, wherein the processor is configured to cause the display device to display or plot the footprint.

17. The system of claim 1, wherein the processor is configured to perform statistical analyses of the footprint to identify the one or more patterns indicative of disordered breathing.

18. The system of claim 1, wherein the processor is configured to perform pattern recognition analyses of the footprint to identify the one or more patterns indicative of disordered breathing.

19. The system of claim 1, wherein the medical device is configured to deliver a therapy and the processor is configured to adjust or titrate the therapy based on the identification of the one or more patterns indicative of disordered breathing.

20. The system of claim 1, wherein the medical device is configured to deliver a therapy and the processor is configured to one or both of determine and monitor effectiveness of the therapy based on the identification of the one or more patterns indicative of disordered breathing.

21. The system of claim 1, wherein the output comprises an alert to a physician or patient based on the assessment of the patient's health status.

22. The system of claim 1, wherein the one or more patterns indicative of disordered breathing comprise a contour of the footprint.

23. The system of claim 1, wherein the processor assessment of the patient's health status comprises assessment of the patient's heart failure status based on the identification of the one or more disordered breathing patterns and the output is based on the assessment of the heart failure.

24. The system of claim 1, wherein the processor assessment of the patient's health status comprises assessment of the patient's disordered breathing status based on the identification of the one or more disordered breathing patterns and the output is based on the assessment of the disordered breathing status.

25. The system of claim 1, wherein the detection circuitry is further configured to detect cardiac signals representative of cardiac electrical activity and the processor is further configured to generate a cardiac activity footprint comprising a mapping having a plurality of contour lines representative of the patient's heart rate variability using the cardiac signals, combine the cardiac activity footprint with the footprint that is generated from the respiration parameter variability, develop a cardio-respiratory index using the combined footprints, and generate one or more outputs based on the cardio-respiratory index.

26. The system of claim 1, wherein the processor is configured to assess a worsening heart failure status based on an increase in size of the one or more patterns of the footprint.

27. The system of claim 1, wherein the processor is configured to assess a worsening disordered breathing status based on an increase in size of the one or more patterns of the footprint.

28. The system of claim 1, wherein the processor is configured to identify at least one of the plurality of contour lines that forms an enclosed loop by itself as a pattern indicative of disordered breathing.

29. The system of claim 1, wherein the medical device is configured for patient implantation and the detection circuitry and the processor are contained within the medical device.

30. A system, comprising:

a medical device comprising sensing circuitry;

detection circuitry coupled to the sensing circuitry, the detection circuitry configured to detect a patient respiration parameter of a patient; and a processor coupled to the detection circuitry, the processor configured to generate a footprint comprising a mapping of a plurality of contour lines representative of the patient's respiration parameter variability using a respiration-modulated signal detected by the detection circuitry, map one or more portions of the footprint to a patient sleep state and a patient wakefulness state, analyze the footprint to identify one or more patterns indicative of disordered breathing, assess the patient's health status based on the analysis of the footprint to identify the one or more disordered breathing patterns, and generate an output based on the assessment of the patient's health status.

* * * * *